United States Patent [19]
Riondel et al.

[11] Patent Number: 5,744,613
[45] Date of Patent: Apr. 28, 1998

[54] PROCESS FOR THE PREPARATION OF ALKYLIMIDAZOLIDONE (METH) ACRYLATES

[75] Inventors: Alain Riondel, Forbach; Jean-Michel Paul, Metz, both of France

[73] Assignee: Elf Atochem S.A., Puteaux, France

[21] Appl. No.: 733,266

[22] Filed: Oct. 17, 1996

[30] Foreign Application Priority Data

Oct. 17, 1995 [FR] France ................ 95 12150

[51] Int. Cl.$^6$ .............. C07D 233/70; C07D 233/80; C07D 233/32; C07D 233/04
[52] U.S. Cl. ........................................ 548/324.1
[58] Field of Search ........................... 548/324.1

[56] References Cited

U.S. PATENT DOCUMENTS

| | | | |
|---|---|---|---|
| 2,871,223 | 1/1959 | Hankins et al. | 260/70 |
| 3,194,792 | 7/1965 | Emmons et al. | 548/324.1 X |
| 3,356,653 | 12/1967 | Sekmakas | 548/324.1 X |
| 4,777,265 | 10/1988 | Merger et al. | 548/320 |
| 4,845,233 | 7/1989 | Higuchi et al. | 548/324.1 |
| 4,859,796 | 8/1989 | Hurtel et al. | 564/204 |
| 5,210,199 | 5/1993 | Grosius et al. | 548/324.1 |
| 5,498,723 | 3/1996 | Riondel et al. | 548/324.1 |
| 5,610,313 | 3/1997 | Riondel et al. | 548/324.1 |

FOREIGN PATENT DOCUMENTS

| | | | |
|---|---|---|---|
| 0236994 | 9/1987 | European Pat. Off. | 548/324.1 |
| 0619309 | 10/1994 | European Pat. Off. | 548/324.1 |

*Primary Examiner*—Floyd D. Higel
*Attorney, Agent, or Firm*—Millen, White, Zelano, & Branigan, P.C.

[57] ABSTRACT

To obtain a compound of formula (I), an anhydride (II) is reacted with a heterocyclic alcohol (III). After the reaction, the excess (meth)acrylic anhydride can be hydrolysed to (meth)acrylic acid by addition of water and heating between 25° and 70° C., preferably between 30° and 50° C., in order to obtain the compound (I) in solution in water and (meth) acrylic acid:

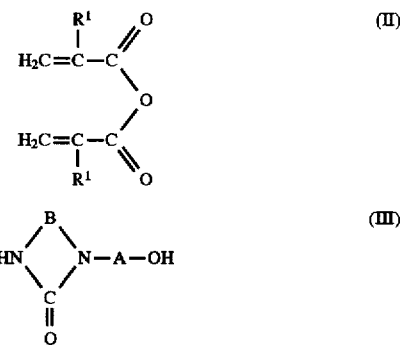

$R^1$=H or $CH_3$; A and B each independently represent a straight- or branched-chain $C_2$–$C_5$ alkylene group.

21 Claims, No Drawings

PROCESS FOR THE PREPARATION OF ALKYLIMIDAZOLIDONE (METH) ACRYLATES

BACKGROUND OF THE INVENTION

The present invention relates to a process for the manufacture of a compound of formula:

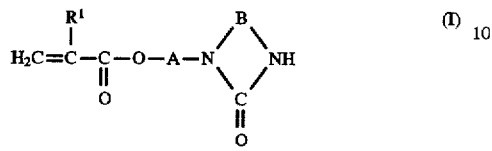

in which:

R¹ represents hydrogen or methyl; and

A and B each independently represent a straight- or branched-chain alkylene group having from 2 to 5 carbon atoms.

These compounds of formula (I) are known for their role in the formation of polymers useful as coatings and adhesives, for the treatment of paper and textiles, in particular by United States Patent U.S. Pat. No. 2,871,223, as well as for their uses as leather treatment agents, and in the production of emulsion paints. Ethylimidazolidone methacrylate (EIOM) is mainly used as wet-adhesion promoter.

The abovementioned United States Patent U.S. Pat. No. 2,871,223 describes the preparation of EIOM by the reaction of 1-(2-hydroxyethyl)imidazolid-2-one (HEIO) with methacryloyl chloride.

EIOM is, however, conventionally prepared by transesterification. Thus, European Patent Applications EP-A-0,236,994, EP-A-0,433,135, EP-A-0,453,638, EP-A-0,571,851 and EP-A-0,619,309 and French Patent Application No. 94-13848 of 18 Nov. 1994, in the name of the Assignee Company, describe the preparation of a compound of the formula (I) defined above, by reaction of at least one (meth)acrylate of formula (IV):

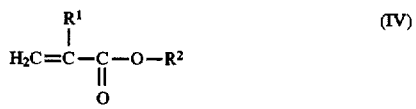

in which:

R¹ represents H or CH₃; and

R² represents a C₁–C₄ alkyl group, with a heterocyclic alcohol of formula (III):

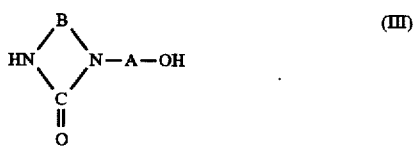

in which A and B have the abovementioned meanings, in the presence of various catalysts or catalytic systems.

These various transesterification processes result in a product of formula (I) being obtained in a form which is suitable only for certain applications. This is in particular the case with EIOM, which is obtained in the form of a solution in methyl methacrylate (MMA).

SUMMARY OF THE INVENTION

The inventors have now discovered that the reaction of the alcohol (III) with (meth)acrylic anhydride makes it possible to obtain, after hydrolysis of the (meth)acrylic anhydride introduced in excess in relation to the alcohol (III), a compound of formula (I) in solution in (meth)acrylic acid and water, which is suitable for new applications.

The subject of the present invention is therefore a process for the manufacture of a compound of the formula (I) as defined above, characterized in that an anhydride of formula (II):

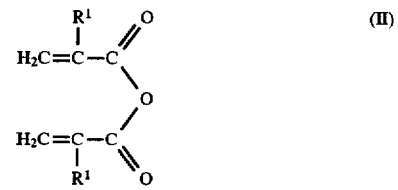

in which R¹ is as defined above, is reacted with a heterocyclic alcohol of the formula (III), also as defined above.

The above reaction can be carried out in the presence of at least one esterification catalyst. Mention may be made, as esterification catalysts, of, for example, Brönsted acids, such as sulphuric acid, alkyl- and arylsulphonic acids or acidic resins containing sulphonic acid groups; Lewis acids, such as boron trifluoride or zinc chloride; or alternatively basic catalysts, such as tertiary amines, for example triethylamine or 1-methylimidazole; as well as the supported forms of these catalysts on solid supports, for example on alumina, active charcoal, silica, acidic resin, and the like.

The amount of catalyst(s) used for the implementation of the process according to the invention is generally approximately between 0.1 and 15% on a molar basis, preferably approximately between 0.5 and 5% on a molar basis, with respect to the alcohol (III).

The reaction of the process according to the invention is advantageously carried out with an anhydride (II)/heterocyclic alcohol (III) molar ratio generally approximately between 1.2 and 10, and preferably between 1.5 and 3.

Moreover, this reaction is preferably carried out while bubbling air through in the presence of at least one polymerization inhibitor used, for example, in the proportion of 0.01 to 0.35% by weight with respect to the weight of the reaction charge. Mention may be made, as examples of polymerization inhibitors which can be used, of, in particular, phenothiazine, hydroquinone monomethyl ether, 2,6-di-tert-butyl-para-cresol, hydroquinone, paraphenylenediamine and their mixtures in all proportions.

The reaction according to the invention is generally carried out at a temperature of between 20° and 120° C., and more particularly between 30° and 90° C., and at atmospheric pressure. The duration of the reaction according to the invention, which obviously depends on the reaction conditions, such as the temperature and the amount of catalyst(s) used, as well as on the nature of the reactants used, is generally approximately between 2 and 15 hours.

After the reaction, the excess (meth)acrylic anhydride is hydrolysed to (meth) acrylic acid by addition of water and heating between 25° and 70° C., and preferably between 30° and 50° C., in order to obtain the compound (I) in solution in water and (meth)acrylic acid.

The hydrolysis can be monitored by quantitative potentiometric determination of the (meth)acrylic acid formed; it generally lasts from 3 to 10 hours.

The following examples illustrate the invention without, however, limiting it. In these examples, the percentages are indicated by weight, except when otherwise indicated.

EXAMPLE 1

Stage 1

178.1 g of methacrylic anhydride, 99.71 g of HEIO, 0.77 g of 2,6-di-tert-butyl-para-cresol and 0.075 g of hydroquinone monomethyl ether as stabilizers and 2.9 g of 1-methylimidazole as catalyst are introduced into a jacketed glass reactor equipped with a probe for measuring the temperature (in the vessel contents), with a variable-speed mechanical stirrer of the anchor type and with a dip tube for introducing air.

The, mixture is brought to 50° C. while air is bubbled through at atmospheric pressure.

The reaction is monitored by thin layer chromatography. The duration of the reaction is 5 hours.

Stage 2

The excess methacrylic anhydride is then hydrolysed to methacrylic acid at 50° C. for 7 hours, the amount of water introduced being 96 g.

This stage is monitored by quantitative potentiometric determination of the methacrylic acid formed.

A product is thus obtained which is provided in the form of a clear, slightly yellow liquid having the following composition:

| | |
|---|---|
| EIOM | 31.5% |
| Methacrylic acid (MAA) | 32% |
| Water | 20% |
| HEIO | 0.3% |
| 2,6-Di-tert-butyl-para-cresol | 2500 ppm |

The conversion of the HEIO, the EIOM yield and the selectivity for EIOM are determined by the following equations from the analysis, by HPLC liquid phase chromatography, of the crude reaction mixture.

Conversion of the *HEIO* (%)

$$C = \frac{\text{Number of moles of } HEIO \text{ converted}}{\text{Number of moles of starting } HEIO} \times 100$$

*EIOM* yield (%)

$$Y = \frac{\text{Number of moles of } EIOM \text{ formed}}{\text{Number of moles of starting } EIOM} \times 100$$

Selectivity for *EIOM* (%)

$$S = \frac{\text{Number of moles of } EIOM \text{ formed}}{\text{Number of moles of } HEIO \text{ converted}} \times 100$$

EXAMPLE 2

Example 1 was repeated, except that the reaction of Stage 1 was carried out at 82° C. without catalyst and while using 0.18 g of phenothiazine as stabilizer.

The results of the tests carried out are given in the table below.

TABLE

| Example | Reaction of Stage 1 Temperature (°C.) | Reaction of Stage 1 Duration (h) | HPLC analysis of the crude reaction mixture from Stage 2 (%) MAA | HPLC analysis of the crude reaction mixture from Stage 2 (%) HEIO | HPLC analysis of the crude reaction mixture from Stage 2 (%) EIOM | C (%) | Y (%) | S (%) |
|---|---|---|---|---|---|---|---|---|
| 1 | 50 | 5 | 32 | 0.3 | 31.5 | 99 | 67.6 | 66 |
| 2 | 82 | 6 | 30.5 | 4.32 | 33.5 | 89.5 | 53.3 | 59.5 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for the manufacture of a compound of formula:

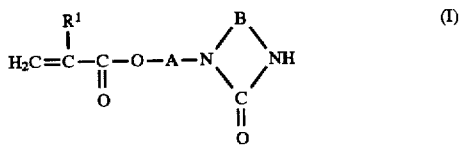

in which:

R1 represents hydrogen or methyl; and

A and B each independently represent a straight- or branched-chain alkylene group having from 2 to 5 carbon atoms, comprising reacting an excess of an anhydride of formula (II):

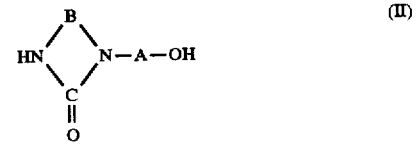

in which R1 is as defined above, with a heterocyclic alcohol of formula (III):

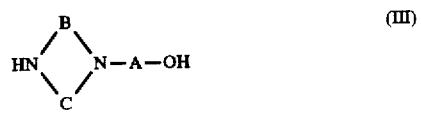

2. A process according to claim 1, characterized in that the reaction is carried out in the presence of at least one esterification catalyst selected from the group consisting of Brönsted acids, Lewis acids, basic catalysts, and supported forms of these catalysts on solid supports.

3. A process according to claim 2, characterized in that the catalyst or catalysts is/are introduced in the proportion of 0.1 to 15% on a molar basis with respect to the alcohol (III).

4. A process according to claim 1 characterized in that the reactants are used in an anhydride (II)/alcohol (III) molar ratio of between 1.2 and 10.

5. A process according to claim 1 characterized in that the reaction is carried out in the presence of at least one polymerization inhibitor used by weight with respect to the weight of the reaction charge.

6. A process according to claim 5, characterized in that the polymerization inhibitor is phenothiazine, hydroquinone monomethyl ether, 2,6-di-tert-butyl-para-cresol, hydroquinone, para-phenylenediamine or mixtures thereof in all proportions.

7. A process according to claim 1 characterized in that the reaction is carried out at a temperature of between 20° and 120° C.

8. A process according to claim 1 characterized in that the reaction is carried out for a duration of 2 to 15 hours.

9. A process according to claim 1 characterized in that, after the reaction, the excess (meth)acrylic anhydride is hydrolysed to (meth)acrylic acid by addition of water and sufficient heating in order to obtain the compound (I) in solution in water and (meth)acrylic acid.

10. A process according to claim 9, characterized in that the hydrolysis is carried for a duration of 3 to 10 hours.

11. A process according to claim 3, wherein said proportion is 0.5 to 5%.

12. A process according to claim 4, wherein said molar ratio is between 1.5 and 3.

13. A process according to claim 7, wherein said temperature is between 30° and 90° C.

14. A process according to claim 9, wherein said heating is conducted at between 30° and 50° C.

15. A process according to claim 2, wherein the catalyst is sulphuric acid, an alkyl arylsulphonic acid or an acidic resin carrying sulphonic acid groups.

16. A process according to claim 2, wherein the catalyst is boron trifluoride or zinc chloride.

17. A process according to claim 2, wherein the catalyst is a tertiary amine or 1-methylimidazole.

18. A process according to claim 2, wherein the catalyst is 1-methylimidazole.

19. A process according to claim 9, wherein the heating is conducted at between 25° and 70° C.

20. A process according to claim 18, characterized in that, after the reaction, the excess (meth)acrylic anhydride is hydrolysed to (meth)acrylic acid by addition of water and sufficient heating in order to obtain the compound (I) in solution in water and (meth)acrylic acid.

21. A composition comprising (A) water, (B) (meth)acrylic acid and (C) a compound of the formula:

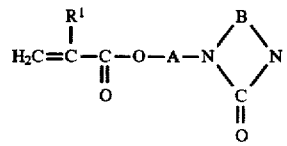

in which:

R$^1$ represent hydrogen or methyl; and

A and B each independently represent a straight- or branched-chain alkylene group having from 2 to 5 carbon atoms.

* * * * *